United States Patent [19]

Pollock

[11] Patent Number: 5,010,001

[45] Date of Patent: Apr. 23, 1991

[54] PREPARATION OF NATURAL OR MODIFIED INSECT TOXINS

[75] Inventor: Thomas J. Pollock, San Diego, Calif.

[73] Assignee: Syntro Corporation, Lenexa, Kans.

[21] Appl. No.: 717,043

[22] Filed: Mar. 28, 1985

Related U.S. Application Data

[63] Continuation-in-part of Ser. No. 573,535, Jan. 25, 1984, abandoned, which is a continuation-in-part of Ser. No. 466,744, Feb. 13, 1983, abandoned.

[51] Int. Cl.$^5$ .................. C12N 1/21; C12N 15/00; C12N 15/32

[52] U.S. Cl. ............................. 435/69.1; 536/27; 435/320.1; 435/252.33; 435/172.3; 935/6; 935/44

[58] Field of Search ............... 435/68, 253, 172.3, 435/317, 832, 849; 536/27; 935/9, 10, 11, 12, 29, 41, 65, 73, 74

[56] References Cited

PUBLICATIONS

Schnepf, H. E. et al., *Proc Natl Acad Sci*, vol 78, pp. 2893–2897, May 1981.

Wong, H. C. et al., *J. Biol. Chem.*, vol. 258, pp. 1960–1967, Feb. 1983.

Moran, C. P. et al. *Cell*, vol. 25, pp. 783–791, Sep. 1981.

Schnepf, H. E. et al., *J. Biol. Chem.*, vol. 260, pp. 6264–6272, May, 1985.

Schnepf, H. C. et al., *J. Biol Chem*, vol. 260, pp. 6273–6280, May, 1985.

Wong, S. H. et al., *Proc. Natl. Acad. Sci.*, vol. 81, pp. 1184–1188, Feb., 1984.

Whiteley, H. R. et al., in *Molecular Cloning and Gene Regulation in Bacillus*, (Ganesan Chang, Hoch, Eds.) pp. 131–144, 1982.

Moran, C. P. et al. *Mol. Gen. Genet*, vol. 186, pp. 339–346, 1982.

Held, G. A. et al., Proc. Natl. Acad. Sci., vol. 79, pp. 6065–6069, 1982.

*Primary Examiner*—Richard A. Schwartz
*Assistant Examiner*—S. Nolan
*Attorney, Agent, or Firm*—Bertram T. Rowland

[57] ABSTRACT

Enhanced production of *B. thuringiensis* delta-endotoxin is achieved by employing the naturally occurring gene where an abbreviated 3'- and 5'-non-coding flanking region is employed. Particularly, the 3'-flanking does not extend past the downstream HincII cleavage site and the 5'-flanking region does not extend past the upstream HincII cleavage site. By having abbreviated flanking regions, enhanced production of the delta-endotoxin in *E. coli* is obtained.

7 Claims, 3 Drawing Sheets

PvuII

```
         10        20        30         40        50         60        70
CAGCTGGCTATGTGACAAAAGAATTAGAOGTACTTCCCAGAAACCGATAAGGTATGGATTGAGATCGGAG
         80        90       100        110       120        130       140
AAACGGAAGGAACATTCATCGTGGACAGCCGTGGAATTACTTCTTATGGAGGAATAATATGCTTTAAAA
        150       160       170        180       190        200       210
TGTAAGTGTGCAAATAAAGAATTACTGACTTGTATTGACAGATAAATAAGGAAATTTTATATGAAT
        220       230       240        250       260        270       280
AAAAAACGGGCATCACTCTTAAAAGAATGTCCGTTTTTTGTATGATTTAACGAGTGATATTTAAATG
        290       300       310        320       330        340       350
TTTTTTTGCGAAGGCTTTACTTAACGGGTACCGCCACATGCCCATCAACTTAAGAATTTGCACTACCCC
        360       370       380        390       400        410       420
CGAAGTGTCAAAAAACGTTATTCTTTCTAAAAGCTAGTAGAAAGGATGACATTTTTATGAATCTTTC
        430       440       450        460       470        480       490
AATTCAAGATGAATTACAACTATTTTCTGAAGAGCTGTATCGTCATTTAACCCCTCTCTTTTGGAAGAA
        500       510       520        530       540        550       560
CTCGCTAAAGAATTAGGTTTTGTAAAAGAAAACGGAAAGTTTCAGGAAATGAATTAGCTACCATATGTA
        570  HcII
TCTGGGTCAGTCGAC
```

FIG. 3

PREPARATION OF NATURAL OR MODIFIED INSECT TOXINS

CROSS REFERENCE TO RELATED APPLICATIONS

This application is a continuation-in-part of application Ser. No. 573,535, filed Jan. 25, 1984, now abandoned, which is a continuation-in-part of application Ser. No. 466,744, filed Feb. 13, 1983, now abandoned, which disclosures are incorporated herein by reference.

BACKGROUND OF THE INVENTION

1. Field of the Invention

Among the best-known of insecticidal bacteria are the numerous strains of Bacillus thuringiensis (BT). The strains differ as to their insecticidal activity, as for example, the strain Kurstaki has killing activity against a number of (but not all) lepidopteran insects in the larval stages, while the Israelensis strains have potent toxicity against a variety of dipteran insects in the larval stages, including mosquitoes and blackflies. The bacterial toxin produced by the BT strain Kurstaki (BTK) has been extensively used as a commercial insecticide against crop pests, particularly the cole crops. In recent years, the Israelensis strain of BT (BTI) has been used to produce a commercial insecticide against mosquitoes.

While the naturally-occurring insecticides have numerous advantages over synthetic insecticides, they have not found extensive use because of the cost of products, due to the complex nutritional requirement of the host. It is therefore extremely desirable to provide improved endotoxins derived from the naturally-occurring endotoxins, which can be produced in more convenient hosts.

2. Description of the Prior Art

Schnepf and Whiteley, Proc. Natl. Acad. Sci. USA (1981) 78:2893-2897 describe the cloning and expression of the Bacillus thuringiensis crystal protein gene in Escherichia coli. Klier et al., The EMBO Journal (1982) 1:791-799 describe the cloning and expression of the crystal protein genes from Bacillus thuringiensis strain Berliner 1715. Held et al., Proc. Natl. Acad. Sci. USA (1982) 79:6065-6069 describe the cloning and localization of the lepidopteran protoxin gene of the Bacillus thuringiensis subsp. Kurstaki. Whiteley et al., describe cloning the crystal protein gene of B. thuringiensis in E. coli in Molecular Cloning and Gene Regulation in Bacilli, Academic Press, 1982, pages 131-144.

Wong et al., J. Biol. Chem. (1983) 258:1960-1967, describe the nucleotide sequence of the promoter region and part of the coding region from BTK HD-1-Dipel.

Milner, R. J., Identification of the Bacillus popilliae group of insect pathogens, pp. 49-59, and Singer, S., Potential of Bacillus sphaericus and related spore-forming bacteria for pest control, pp. 283-298, In Microbial Control of Pests and Plant Diseases, 1970-1980, ed. H. D. Burges, Academic Press, N.Y. 1981.

SUMMARY OF THE INVENTION

Methods and compositions are provided concerned with polypeptide pesticidal toxins, based on naturally occurring endotoxins. The polypeptide toxins have at least a substantial proportion of the amino acid sequence of a naturally occurring endotoxin. The polypeptides are produced by the introduction of chimeric DNA into an appropriate prokaryotic host, where the chimeric DNA includes transcriptional and translational regulatory sequences functional in the host and a coding sequence under the regulatory control of the regulatory sequences coding for the polypeptide toxin. The polypeptide toxins find use as insecticides.

BRIEF DESCRIPTION OF THE DRAWINGS

FIG. 3 is the nucleotide sequence between the downstream PvuII site and the HincII sites of the restriction map in FIG. 2.

DESCRIPTION OF THE SPECIFIC EMBODIMENTS

Figure 1:
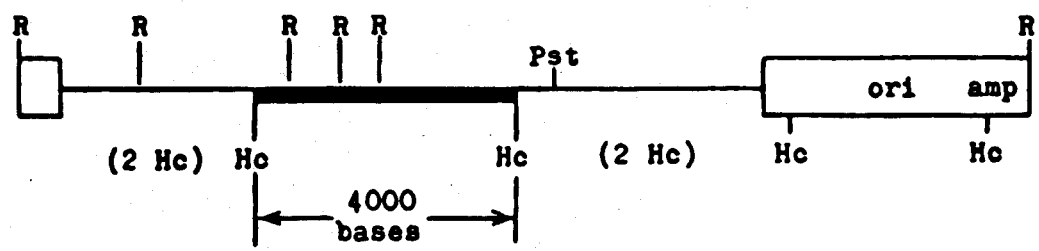
FIG. 1 is a restriction map of pSY112. The insert of BTK DNA is represented as a single line; pBR322 is a double line. Additional unmapped restriction sites are shown in parentheses. The heavy line shows the region that was cloned in pSY177 and pSY176. The abbreviations are: R=EcoRI, Pst=PstI, Hc=HincII, ori=origin of replication for plasmid pBR322, amp=ampicillin resistance gene.

Novel methods and compositions for producing toxins are provided based on the naturally-occurring endotoxins of Bacillus, e.g., thuringiensis, popilliae, sphaericus, particularly strains of species of B. thuringiensis. Various species of B. thuringiensis include Kurstaki, Israelensis, Dendrolimus, Berliner, Aizawa, etc. The various strains produce a crystalline protein which serves as an endotoxin, the endotoxin from different strains having differing specificity. The genes encoding the endotoxin have been found in a number of situations on plasmids and in some instances on both plasmids and chromosomal DNA.

In accordance with the subject invention, plasmid or chromosomal DNA may be isolated from an appropriate host and the gene or genes expressing the endotoxin isolated. The fragment containing the gene of interest may be subcloned and the clone containing the fragment of interest may be detected using Northern blots, Western blots, antibodies to the toxin, or the like. Various techniques may be employed for detecting the gene of interest and a number have been described in the literature.

The sequences coding for the endotoxin including flanking sequences may be manipulated in a variety of ways to achieve a variety of purposes. The manipulations may involve removal of flanking sequences and providing alternative regulatory sequences heterologous to the coding sequence. (By heterologous is intended that the flanking regions are not naturally found with the coding sequence, when heterologous is employed for comparing polynucleotide sequences.) All or a portion of the 5'- and 3'- flanking regions may be removed, so that there may be retention of immediately adjacent untranslated sequences, which may extend to include transcriptional and/or translational regulatory signal sequences. Modifications may also be made in the coding sequence. The modifications may involve deletions, insertions, combinations thereof, as well as substitutions, where the variations may involve as much as about 40 mole percent of the molecule. Changes, such as deletions may involve the internal regions, particularly regions from about the XmnI restriction site located between a HindIII site and a BclI site or the N-terminal region, where such region will generally lack not more than about 40, usually not more than about 30, amino acids in the N→C direction and the C-carboxy region should generally include substantially all of the amino acids from the C-terminus to the first, preferably to the second PvuII site and may include the flanking region extending to the KpnI site in the untranslated region, or beyond, e.g., the HincII site. Instead of deletions, substitutions may be employed, where the substituted amino acid sequence will usually be not more than about two-fold greater, preferably not more than about 1.5-fold greater, and more preferably not more than 1-fold the number of amino acids present at the site. Insertions may be introduced for a variety of reasons, providing for enhanced stability of the toxin, varying the toxin host range, either increasing or decreasing the range, providing for improved ease of formulation, or the like.

The deletions, substitutions, mutations, or the like, may be performed in a variety of ways. Deletions can be achieved by partial or complete digestion, depending on the presence or absence of the unique restriction site, where the presence of more than one restriction site, can result in a deletion, while the presence of a unique restriction site can be expanded by restriction at the unique site and treatment with an exonuclease, such as Bal31. By employing varying times for the Bal31 resection, differing amounts of DNA may be removed. By ligation, cloning and sequencing of the resulting sequence, the presence or absence of an open reading frame can be determined. Alternatively, different restriction enzymes may be used so as to provide for deletion of regions between the different restriction sites. Restriction with different restriction enzymes may be coupled with exonuclease digestion to further expand the deletion. Alternatively, in vitro mutagenesis may be employed, where the oligonucleotide sequence provides for the absence of nucleotides, transitions or transversions, the insertion of nucleotides, or the like. By employing primer repair, one can also provide for insertions, deletions, and mutations and, furthermore, define a blunt-ended border beginning within the coding sequence. Usually, fewer than one-third, more usually, fewer than about one-quarter of the nucleotides will be deleted, while deletions in the coding region will usually involve at least three nucleotides and multiples thereof.

Areas of particular interest for insertion, deletion, or substitution, include the N-terminus, particularly the first 90 bases of the coding sequence, and the region between the upstream HindIII site and the second PvuII site in the 5'-3' direction of transcription, more particularly the first PvuII site.

The endotoxin gene has its own promoter and regulatory system, so that the 5'-terminus can include a bacterial promoter, which allows for expression in Bacillus, as well as other bacteria, e.g., E. coli. By appropriate choice of restriction sites, one can cleave upstream from a promoter region and provide a fragment having an intact promoter region, ribosomal binding site and the endotoxin structural gene with a portion of the noncoding 3' region. A DNA fragment having the regulatory sequences for expression and a structural gene encoding for a toxin may now serve as a source of the toxin by introduction of the fragment into an appropriate host under conditions where the DNA fragment may be replicated, the host proliferated and the endotoxin expressed. One may manipulate the coding sequence so as to provide for a polypeptide different from the natural endotoxin, but retaining insecticidal activity.

The 3'-terminus may be downstream from the PvuII site so as to provide a complete gene with one or more stop codons. However, conveniently an abbreviated flanking region is retained where a few base pairs downstream from the stop codon are present, which may or may not include a terminator site. Conveniently, the 3'-terminus will be fewer than about 300 bp from the stop codon(s), usually fewer than about 200 bp, and may be fewer than 100 bp from the stop codon(s). Substantial enhancements in yield are achieved without removing all of the 3'-flanking region. On the 5' side of the toxin coding sequence, the HincII site is located about 150 bases from the translational start. Substantial enhancements in yield are achieved by retaining the 5'-flanking regions between the 5' HincII site and the start of translation.

If desired, one may remove the endogenous promoter and introduce promoters from other genes, as well as other sequences for providing desired properties or functions, particularly where codons are removed from the 5'-end of the coding region. By defining a ribosomal binding site sequence adjacent and upstream from an f-met codon, one can define the initiation site of the endotoxin gene. Once these sites are defined, one can manipulate the 5'-end of the gene for changing the promoter or introducing various signals. A wide variety of promoters may be employed, particularly prokaryotic promoters, which by themselves or in conjunction with other regulatory signals, may provide for regulated transcription, semi-constitutive or constitutive transcription, temperature-sensitive regulation, or the like. Cooperating sequences may be involved in repression, derepression, activation, enhancement, or the like, providing sequences such as operators, initiators, and the like.

Besides regulatory sequences providing for control of transcription, other sequences may be introduced, involved with translation and processing to provide a mature product. Sequences which may be included provide for enhanced stability of the messenger RNA, processing through the secretory apparatus and processing of the leader sequence to remove the sequence from the N-terminus to provide for the mature endotoxin, etc.

The constructs of this invention will for the most part have the following formula:

$$[(RS)_a\text{-}(P)_b\text{-}RBS\text{---}]_c\text{-i.c.-}(L\&PS)_d$$

$$(mETG)_s\text{.c.-nbp}$$

wherein:

RS refers to regulatory sequence as described above, which while indicated as upstream from P, may in fact, be on either side of P;

P intends an RNA polymerase binding site, normally referred to as a promoter;

RBS intends the ribosomal binding site, sometimes referred to as the "Shine-Dalgarno" binding site;

i.c. intends the initiation codon, f-met;

L&PS intends leader and processing sequences, involving DNA sequences encoding for secretion of the protein and processing for removal of the leader sequence to provide for the mature endotoxin;

mETG intends the endotoxin gene, which is provided with a limited 3'-flanking region;

nbp intends the number of base pairs extending from the stop codon(s) of the gene, n ranging from 0, usually from at least 50, more usually at least 75, and not more than about 300, usually not more than about 200;

s.c. intends one or more stop codons for termination of translation;

a is 0 or 1;

b is at least 1 and will generally be from about 1 to 2, that is there may be more than one promoter;

c is 0 or 1; and d is 0 or 1, the leader and processing signal being either respectively absent or present.

The various sequences providing for the regulation of transcription and expression may come from the same or diverse sources. Primarily, the sequences will come from prokaryotic sources which will be Escherichia or Bacillus sources, *E. coli, B. thuringiensis*, or *B. subtilis*.

The modified DNA fragment encoding for deltaendotoxin may be cloned to provide for multiple copies, allow for further manipulation, particularly at the 5'-terminus or internal sequence, and may then be introduced into an appropriate expression vector.

As already indicated, one may use primer repair by employing an oligonucleotide complementary to the sequence of the endotoxin gene which is to serve as the 3'-terminus of the endotoxin gene. The oligonucleotide used as the primer would generally be at least 8 nucleotides, more usually at least 10 nucleotides, and may be 12 nucleotides or more. By cloning the endotoxin gene in an appropriate vector, denaturing the DNA to provide single stranded DNA and then hybridizing with the primer oligonucleotide, DNA polymerase I will replicate the endotoxin gene, while removing the nucleotides extending as an overhang downstream from the primer oligonucleotide.

In addition or as an alternative, one may use in vitro mutagenesis, where an oligonucleotide is provided which has a deletion, insertion, or one or more point mutations, so that upon hybridizing with a single strand of the endotoxin gene, the gene will be replicated incorporating the differences in one of the strands which are present in the oligonucleotide employed as the primer. This technique can be conveniently used for introducing restriction sites at precise positions which will allow for introduction of deletions in or truncating of the endotoxin gene and providing a convenient terminus for ligation to another DNA sequence, for example, regulatory sequences at the N-terminus or translational or transcriptional terminators and stabilizing inverted repeat sequences at the C-terminus.

Where a convenient restriction site exists, but is upstream from the desired terminus, a synthetic adapter can be employed which complements the restricted terminus, replaces the lost base pairs and provides a new 3'-terminus for linking to the downstream DNA sequence. Desirably, the adapter should have different termini to ensure the proper orientation.

The particular vector will depend upon the host. Since the endotoxin gene is bacterial, a prokaryote will be the preferred host. Therefore, the expression vector of choice will be a vector capable of replication in a prokaryote, e.g., *Bacillus subtilis, E. coli*, etc. and derived from a plasmid or phage native to the prokaryote. See, for example, U.S. Pat. No. 4,419,450 and references cited therein. Once the endotoxin gene has been inserted into the expression vector, where the fragment containing the endotoxin or modified endotoxin structural gene (collectively "toxin" gene) may include its own promoter or the promoter may be appropriately situated in the vector or introduced after insertion of the gene, the resulting expression vector may be used for introduction into a prokaryotic host.

Various vectors may be employed, such as cosmids, plasmids, or phage. Depending upon the nature of the vector, various techniques may be employed for introducing the DNA into the host to provide for maintenance of the episomal element, integration, or a combination of the two. Frequently, high copy number vectors will be employed, having copies of at least 10, preferably 20 or more. Methods for introducing DNA constructs include transformation, conjugation, transfection and transduction. Host cells or protoplasts may be employed.

Vectors can be made employing the replication system from prokaryotic plasmids, e.g., *E. coli* or Bacillus plasmids, cryptic plasmids. See, for example, LeHegarat and Anagnostopoulos, infra. Desirably, the expression vector will have one or more, preferably two or more, unique restriction sites in non-essential regions, particularly in a marker, where there are two or more markers providing for selection. Desirably, the expression vector should be less than about 15 kbp, more preferably less than about 10 kbp. Markers may include antibiotic or other toxin resistance, complementation in an auxotrophic host, immunity, etc. In some instances, it may be desirable to have vector integration into the host chromosome, so that the functioning gene expressing the modified endotoxin is stably maintained in the chromosome and/or on episomal elements.

Various prokaryotic hosts may be used such as species of Rhodopseudomonas, Pseudomonas, Erwinia, and Bacilli other than *Bacillus thuringiensis*, such as megaterium or the other Bacillus species indicated previously.

The cells into which the toxin gene is introduced are then grown and the toxin produced. The bacteria, normally dead, may be used directly or the protein may be obtained by lysis of the host and isolation of the toxin protein. Where a leader sequence is provided, the toxin will be secreted into the nutrient medium and may be prepared by conventional techniques, e.g., filtration, chromatography, spray drying.

Alternatively, the crystal protein may be produced by fermenting the natural strain and those related to *Bacillus thuringiensis kurstaki*. The cells normally undergo sporulation and lysis releasing the crystal protein. This can be solubilized by treatment with alkali and reducing agents to pH values usually 9 or higher. The soluble crystal protein can then be digested with trypsin to increase the specific activity. The activation is usually a factor of at least four-fold, sometimes eight-fold.

The bacteria containing the protein or the protein may be formulated in conventional ways for the naturally-occurring endotoxin. See, for example, Johnson, *J. of Economic Entomology* (1982) 75:207–210, which disclosure is incorporated herein by reference. Formulations may include a variety of additives such as extenders, detergents, wetting agents, stabilizers, polymers, other toxins, sunscreens, e.g., carbon black, or the like. Of particular interest is the use of bait as an attractant or feeding stimulant, e.g., cottonseed or soybean meal with molasses or lactose. Such additives are available commercially as Coax (Traders Oil Mill Co., Fort Worth, Tex.) and Gustol (Sandoz, Inc., San Diego, Calif.).

The formulation may be dry powder, suspension, etc. The formulation may be applied as a powder, liquid spray, or other convenient means. The formulation will vary widely as to percentages, depending upon how the formulation is to be applied and the dilution employed. Generally, the endotoxin will be applied at about 0.05 to 1 lb./acre, more usually about 0.1 to 0.5 lb./acre. The weight ratio of endotoxins to formulated stimulant will be about 1:5-10.

The modified toxins of the subject invention provide for a variety of advantages. In a number of instances, the compounds are found to have higher toxin activity on a weight and/or mole basis. The smaller toxin molecules provide for economies of production on a mole basis. In addition, where it is desirable that the protein be isolated in soluble form for a subsequent manipulation or formulation, the modified toxins provide for soluble proteins, which may be readily formulated.

Enhanced activity of the expression product of the BTK endotoxin gene (the 130 kD crystal protein) can be achieved by solubilizing the crystalline protein obtained in crystalline form or isolating the protein if soluble by any conventional means. The means may involve treatment with a reducing agent, such as dithiothreitol or β-hydroxyethyl mercaptan and then dialyzing the solubilized protein against an appropriate buffer at a mildly alkaline pH, about 9-10. The solubilized protein is then treated with the protease trypsin or protease having substantially the same specificity in a weight ratio of about 0.1 to 2 weight percent of enzyme based on solubilized protein, conveniently under conditions specified by the protease supplier, for a time sufficient to maximize the production of a polypeptide of about 55-60 kD. This will generally be from about 20 to 40 minutes. At the end of this time, the product may then be purified if desired, and may be used as the toxin.

The following examples are offered by way of illustration and not by way of limitation.

EXPERIMENTAL

1. Construction of a Library of Cloned Fragments of BTK Plasmid DNA

Plasmid DNA was prepared from BTK strain HD-1 (Dulmadge, *J. Invertebr. Path.* (1970) 16:385-389) grown in Difco Antibiotic Medium 3 to a cell density equivalent to an $OD_{600}$ of 0.8. Cells were harvested by centrifugation and resuspended for lysis according to the method of Birnboim and Doly, *Nucleic Acids Res.* (1979) 7:1513. This involved treatment with egg white lysozyme, sodium dodecyl sulfate (SDS) and NaOH, followed by precipitation of the high molecular weight chromosomal DNA with sodium acetate in the cold. The precipitated chromosomal DNA was centrifuged to the bottom of the tube so that the cleared supernatant contained mostly plasmid DNA. The plasmid DNA was recovered by precipitation with one volume of isopropanol and then by two volumes of 95% ethanol. The closed-circular plasmid DNA molecules were purified by sedimentation in equilibrium density gradients of CsCl containing ethidium bromide. The lower band in the gradient was removed, extracted repeatedly with butanol to remove the ethidium bromide, and the DNA was then concentrated by precipitation with ethanol.

The plasmid DNA was separated into fractions enriched for different size classes by velocity sedimentation. Plasmid DNA was layered onto a preformed sucrose gradient (10–40% W/V) and centrifuged for 4 hours at 40,000 rpm in a Beckman Ti50 rotor. The rapidly sedimenting DNA from the lower one-half of the gradient was pooled and concentrated by precipitation with ethanol. Large fragments of DNA were then prepared for cloning. The BTK DNA enriched for large plasmids was digested partially with the restriction enzyme Sau3A. The fragments were separated into size classes by velocity sedimentation on a pre-formed sucrose gradient (10–40% W/V) that was centrifuged 4 hours at 50,000 rpm in a Beckman Ti50 rotor. The DNA fractions were concentrated by precipitation with ethanol. As shown by analytical agarose electrophoresis, the fraction selected for further use contained fragments of about 10 kilobase pairs (kbp) in length.

The vector plasmid pBR322 was grown by amplification with chloramphenicol in minimal medium (Clewell and Helinski, *J. Bacteriol.* (1972) 110:1135). The DNA was purified by the method of Birnboim and Doly, supra, including equilibrium sedimentation in CsCl density gradients containing ethidium bromide (Maniatis et al., (1982) *Molecular Cloning*, CSH Laboratory, N.Y., p. 93). For cloning of the Sau3A digest of large plasmids from BTK, the pBR322 vector was digested with BamHI restriction endonuclease to generate ends complementary to those generated by Sau3A. The BamHI was removed by phenol extraction and the DNA concentrated by precipitation with ethanol.

The BamHI-digested pBR322 and the Sau3A-generated fragments of BTK large plasmids were mixed in approximately equal amounts to allow hybridization of the complementary ends. Ligation was carried out with T4 DNA ligase according to the conditions suggested by the manufacturer (Bethesda Research Laboratories, Inc.). A portion of the ligated DNA was used to transform $CaCl_2$-treated *E. coli* strain HB101 (Mandel and Higa, *J. Mol. Biol.* (1970) 53:154). Transformed cells were incubated for 30 min at 37° C. in LB medium (Maniatis et al., supra, p. 68) and then spread onto agar plates containing LB and ampicillin at 20 μg/ml and grown 24 h at 37° C. Ampicillin-resistant isolates were streaked onto agar plates containing LB and tetracycline at 20 μg/ml. Small cultures in LB were grown of each isolate that was ampicillin-resistant and tetracycline-sensitive. The Birnboim-Doly plasmid-isolation procedure was scaled down volumetrically in order to compare the sizes of the plasmids with inserts to the pBR322 vector alone on analytical 0.8% agarose gels (Maniatis et al., supra, pp. 150-172). Insert sizes as large as 15 kbp were obtained, and these constituted the library of cloned fragments derived from the large plasmids of BTK.

2. Identification of the Toxin-Producing Derivative of HB101

The delta-endotoxin of BTK was purified from cultures grown 7 days in Difco Antibiotic medium 3 at 30° C. with vigorous aeration. The sporulated culture contained lysed cells, toxin-crystals and spores. The pH of the culture was neutralized with HCl and particulate material concentrated twenty-fold by centrifugation and stored at −20° C. The procedure for toxin-crystal purification was adapted from Ang and Nickerson, *Appl. Environ. Microbiol.* (1978) 36:625–626. Culture samples of 5 ml were layered onto step gradients of NaBr in water. The gradients consisted of an underlayer of 20 ml having a refractive index of 1.395 and an overlayer of 20 ml having a refractive index of 1.383. The gradients were centrifuged in a Sorvall HB4 rotor at 8,000 rpm for 90 min at 4° C. The band in the middle of the gradient was enriched for crystal protein, while most of the spores were pelleted. The banded crystals were diluted with one volume of water and pelleted in the Sorvall SS-34 rotor at 5,000 rpm for 5 min at 4° C. The pellet was dissolved in 10 ml of NaBr with a refractive index of 1.389 and centrifuged for 15 h at 35,000 rpm in Beckman SW41 rotor at 15° C. Again, the midband of crystals was collected as before. Electrophoresis of a small aliquot in a polyacrylamide gel containing SDS showed that about 95% of the total protein stained by Coomassie brilliant blue dye migrated at the position of a 130,000 Dalton (dal) polypeptide when compared to the standard proteins myosin and $\beta$-galactosidase. Most of the residual protein banded at the position of a 65,000 dal species or failed to enter the gel.

A second easier method was devised to purify the delta-endotoxin. The particulate material from a sporulated culture of BTK grown as described above was washed 2 times with 1M NaCl and collected each time by centrifugation in the Sorvall SS-34 at 12,000 rpm for 5 min at 4° C. This was followed by a single wash with 0.1M NaCl. The pelleted material was resuspended in 10 ml of water and 1N NaOH was added dropwise until pH 12 was reached. After 5 min at room temperature, β-mercaptoethanol was added to 0.1% V/V. Microscopic examination showed that the crystals were dissolved, but not the cell debris and spores. The latter was pelleted by centrifugation in the Sorvall SS-34 at 12,000 rpm for 5 min at room temperature. The supernatant was saved, adjusted to pH 8 with HCl and then buffered to a final concentration of 0.1M Tris-HCl, pH 8. A final centrifugation was performed in the Sorvall SS-34 at 12,000 rpm for 5 min at room temperature. The supernatant was stored at −20° C. and contained solubilized crystal protein of about 95% purity. Both preparations of toxin protein were used to stimulate anti-toxin antibody production in rabbits.

The purified toxin protein in both crystal or solubilized form was injected subcutaneously along with Freund's complete adjuvant at about 6 sites on the back of mature New Zealand rabbits. After 4 weeks, the rabbits were inoculated again with toxin protein in Freund's incomplete adjuvant and thereafter every 2 weeks. Blood was collected from the ear veins about 6 weeks after the original injection. The blood was allowed to clot at 4° C. for 16 h. The serum was removed and stored at −20° C. This serum cross-reacted in Ouchterlony tests with the most purified crystal protein preparations.

In order to apply the indirect radioimmunoassay scheme devised by Erlich et al., *Cell* (1978) 13:681-689 to identify toxin-producing clones, some of the serum was used to prepare the $F(ab')_2$ fragment of the antitoxin antibody in the serum. The IgG fraction of the serum was purified by ammonium sulfate precipitation (Garvey et al., (1977) *Methods in Immunology,* W. A. Benjamin, Inc., Reading, Mass., pp. 218-219), followed by passage through DEAE-AffiGel-Blue according to the manufacturer's instructions (Bio-Rad Laboratories, Inc.). The IgG fraction was digested with pepsin (Garvey et al, supra, pp. 263-264) and both the free Fc portions and the uncleaved antibody containing Fc were removed by binding to protein A-Sepharose CL-4B according to the instructions of the manufacturer (Pharmacia Fine Chemicals). The material passing through the column was the purified $F(ab')_2$ fragment of the antibody and was used in the indirect radioimmune assay (IRIA).

The IRIA was adapted from the assay described by Erlich et al., supra. First, 50 μl of a solution of $F(ab')_2$ containing about 1 to 1.5 μg protein in 0.15M phosphate-buffered saline pH 7.4 (PBS) was incubated in each well of a polyvinyl chloride microtiter plate (Cooke Laboratory Products) for 2 to 16 h at room temperature or 37° C. Any residual solution was aspirated and replaced with 200 μl 3% (W/V) bovine serum albumin (BSA, fraction V from Sigma Chemicals). After 1 to 2 h at room temperature, the BSA was aspirated. The wells were then ready for addition of crude lysates of bacterial cultures.

Cell cultures to be tested for production of antibody-reactive material were processed as follows: About $10^9$ logarithmically growing cells in LB medium were concentrated by centrifugation and resuspended in 10 mM Tris-HCl, pH 8, with 1 mM EDTA. Egg white lysozyme was added to 1 mg/ml and the mixture incubated at 37° C. for 30 min followed by 3 cycles of freezing-thawing in a dry ice-ethanol bath. The lysates were then treated with final concentrations of 4 mM phenylmethylsulfonylfluoride, 10 mM $MgCl_2$ and 10 μg/ml pancreatic DNase to reduce proteolysis and viscosity. The lysates were vortexed and then 50 μl samples were dispensed to $F(ab')_2$-coated wells. After 1 h at room temperature, the wells were aspirated and washed once again with PBS, twice for 5 min with 0.1% (V/V) Tween 20 in PBS and once again with PBS. Anti-toxin serum (50 μl) diluted 100-fold with PBS was placed in the wells for 60 min at room temperature. A washing cycle as described above followed. Lastly, 45 μl of PBS and 5 μl of $^{125}I$-protein A (New England Nuclear, 2-10 μCi/μg) were incubated in the wells for 20 min at room temperature. The wells were washed as above, cut out and counted by liquid scintillation. The positive clones showed signal to background ratios of about 3:1. Strain HB101 carrying the vector pBR322 served as the background control. These counts were averaged and then subtracted from the positive controls and samples being screened. For standards, varying amounts of purified solubilized toxin is added to lysates of HB101 carrying only the vector pBR322. The number of cells is kept constant for each sample tested. The results for two experiments are given in Table 1. Only the positive standards and the original clone of the BTK toxin gene are included. In some instances a nonreproducible positive signal was detected, however pSY112 was consistently positive as shown. Based on the data in Table 1, where $1.6 \times 10^9$ bacteria are applied to a sample well and assuming that there are 0.5 picograms of protein per cell, HB101 carrying pSY112 produces about 0.02% of its cellular protein as antigen.

TABLE 1

IDENTIFICATION OF BTK CLONE

| Plasmid | Toxin added (ng) | Counts bound | Counts above average background |
|---|---|---|---|
| (Exp. 1) | | | |
| pBR322 | 0 | 2552 | 0 |

TABLE 1-continued

IDENTIFICATION OF BTK CLONE

| Plasmid | Toxin added (ng) | Counts bound | Counts above average background |
|---|---|---|---|
|  | 0 | 2438 |  |
|  | 20 | 2839 | 228 |
|  | 20 | 2608 |  |
|  | 40 | 3392 | 939 |
|  | 40 | 3476 |  |
| pSY112 | 0 | 4190 | 1928 |
|  | 0 | 4657 |  |
| (Exp. 2) |  |  |  |
| pBR322 | 0 | 1860 | 0 |
|  | 0 | 1613 |  |
|  | 40 | 2195 | 460 |
|  | 40 | 2198 |  |
|  | 160 | 3405 | 1650 |
|  | 160 | 3992 |  |
| pSY112 | 0 | 3130 | 1696 |
|  | 0 | 3597 |  |
|  | 0 | 3569 |  |

To verify that a given clone produced a toxic protein, larvae of *Trichoplusia ni* were fed with medium containing lysates of bacterial cultures. The lysates were prepared as for the IRIA, bit with the PMSF omitted, and were mixed at different dilutions with growth medium according to method adapted from Dulmadge et. al., *J. Invertebr. Path.* (1970) 15:15-20; Dulmadge et al., *U.S. Dep. Agric. Tech. Bull.* (1976) 1528:1-15. The assays were scored for killing by eye and larvae size by weighing the larvae after 4 to 7 days. The toxicity data for the original clone, pSY112, is included in part (5) below. The toxicity is consistent with there being less than 0.1% of the cell protein as toxin for strain pSY112, as shown with the IRIA.

3. Characterization of the Cloned DNA in Plasmid PsY112

The hybrib plasma, pSY112, has an insert of about 9600 base pairs of DNA derived from the Sau3A-digested large plasmids of BTK. The insert is at the BamHI site in the tetracycline-resistance gene of the vector plasmid pBR322. Thus, pSY112 confers ampicillin-resistance, but cells containing this plasmid are tetracycline-sensitive. Hybridization tests by Southern blot analysis show that nick-translated labeled pSY112 DNA is complementary, as expected to a single large plasmid (70 kD) of BTK.

A partial restriction map of pSY112 is given FIG. 1. The heavy line in FIG. 1 shows the region subcloned in pSY177 and pSY176 as described in part (4) below.

4. Subcloning and DNA Sequences of the BTK Toxin Gene

A fragment of about 4000 base pairs and bounded by the HincII restriction sites was removed from pSY112 and subcloned into the Hincll site within the tetracycline-resistance gene of plasmid pBR322. After transformation into *E. coli* HB101 both fragment orientations (pSY177 and pSY176) are equally active for antigen production as tested by IRIA and toxicity to the larvae of *Trichoplusia ni* (cabbage looper) in diet incorporation assays. Table 2 below shows the results of the IRIA analysis of antigen production by strain HB101 carrying plasmids pBR322, pSY112, pSY177 and pSY176. Given the variance in the data points, the "Counts above average background" for pSY112, 177 and 176 are probably about equal within the margin of error. These IRIA results do show a saturation effect, but in other quantitative analyses (see section 5 below) both pSY177 and pSY176 make more toxin protein than does pSY112.

TABLE 2

ANTIGEN PRODUCTION BY SUBCLONES

| Plasmid | No. of cells in well ($\times 10^{-6}$) | Counts bound | Counts above average background |
|---|---|---|---|
| pBR322 | 25 | 1011 | 0 |
| | 25 | 968 | |
| | 5 | 817 | 0 |
| | 5 | 897 | |
| pSY112 | 25 | 2579 | 2316 |
| | 25 | 2053 | |
| | 5 | 2292 | 1945 |
| | 5 | 1598 | |
| pSY177 | 25 | 2146 | 2734 |
| | 25 | 3322 | |
| | 5 | 3378 | 3451 |
| | 5 | 3525 | |
| pSY176 | 25 | 2780 | 2617 |
| | 25 | 2455 | |
| | 5 | 3150 | 2742 |
| | 5 | 2334 | |

5. Amount of Toxin Accumulated by Subclones

Both pSY177 and pSY176 plasmid bearing derivatives of *E. coli* HB101 produce about 20 to 50 times more toxin activity than the original construction pSY112 as judged by the bioassay with *T. ni.* A comparison of the toxicity for strain HB101 carrying plasmids pSY112, pSY177 and pSY176 is shown in the following Table. The weight of ten larvae was measured after five days exposure and feeding on the diet containing different concentrations of cells from the test cultures. A "Relative Concentration" of 1 is equal to $1\times10^7$ cells added to about 20 ml of insect diet.

TABLE 3

TOXICITY TO TRICHOPLUSIA NI LARVAE

| Sample | Relative concentration of cells in diet | weight of 10 larvae (g) |
|---|---|---|
| pBR322 | 1 | 1.3 |
| | 3 | 1.1 |
| | 10 | 1.3 |
| | 30 | 0.9 |
| | 100 | 1.0 |
| | 300 | 0.7 |
| pSY177 | 1 | 0.45 |
| | 3 | 0.3 |
| | 10 | 0.1 |
| | 30 | 0.05 |
| | 100 | 0.03 |
| | 300 | 0.03 |
| pSY112 | 1 | 1.0 |
| | 3 | 1.0 |
| | 10 | 0.9 |
| | 30 | 0.7 |
| | 100 | 0.35 |
| | 300 | 0.1 |
| pSY176 | 1 | 0.5 |
| | 3 | 0.5 |
| | 10 | 0.1 |
| | 30 | 0.05 |
| | 100 | 0.03 |
| | 300 | 0.03 |

To measure the amount of 130 kD toxin protein present in cell extracts, samples were electrophoresed through a denaturing SDS polyacrylamide gel to separate the proteins by approximate size. Samples of different concentrations of purified 130 kD crystal toxin protein were electrophoresed in adjacent lanes of the gel. The gel was then stained with Coomassie dye to visualize the proteins. The amount of 130 kD protein accumulated by the subclones, pSY177 and pSY176, was determined by comparison to the standards by eye. About 1 to 2% of the cell protein in strain HB101 carrying plasmid pSY177 and pSY176 is the 130 kD product of the subcloned toxin gene.

A Western blot analysis indicating the sizes of the antigenic polypeptides accumulating in these four strains was made. Antiserum was raised against the denatured form of the 130 kD full size BTK toxin protein isolated from purified crystals. Strains pSY112, 177 and 176 each show an antigen of 130 kD that is not seen for the pBR322 negative control strain.

Figure 2:
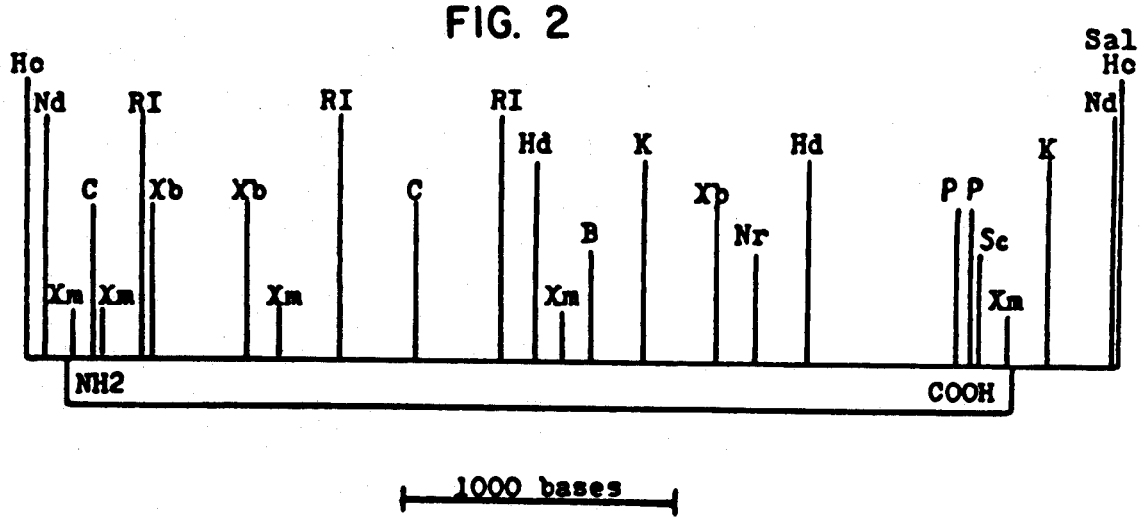
FIG. 2 is a restriction map of the 4000 base pair HincII fragment of plasmid pSY112. The restriction sites are abbreviated: Hc=HincII, Nd=NdeI, Xm=XmnI, C=ClaI, R=EcoRI, Xb=XbaI, B=BclI, K=KpnI, Nr=NruI, Sc=ScaI, P=PvuII, Sal=SalI.

Therefore, the 4000 base pair fragment includes a promoter and ribosome binding site that are functional for gene expression in E. coli. The orientation for pSY177 is the same as for pSY112 with respect to flanking markers on pBR322; pSY176 is in the opposite orientation. A detailed restriction map confirmed by sequencing portions of the 4000 base pair insert is given in FIG. 2.

The control region and the start of the structural gene are located in the region to the extreme left bounded by the NdeI and ClaI restriction sites. The gene is transcribed from left to right on the map. The C-terminal end of the full length (130 kD) structural gene is located on the extreme right side of the map between the PvuII and KpnI sites. The extent of the full length (130 kD) BTK structural gene is shown by the double line in FIG. 2.

The DNA sequences of the BTK toxin gene are displayed in the Figure. They were determined by standard chemical techniques (Maxam and Gilbert) or by dideoxy (primer extension) methods. The first sequence begins at the left HincII site and continues to the rightmost XbaI site. The portion between the left HincII site and the middle EcoRI site was published by Wong et al., (J. Biol. Chem., 258:1960–1967, 1983). Their sequence is included for the region between the left HincII and EcoRI sites, as it matches the sequence determined in this investigation exactly between the left HincII and ClaI sites. The amino acids coded by this sequence are also shown.

The C-terminal sequences between the downstream PvuII site and the HincII site are given in FIG. 3. These sequences were determined as described above.

The exact sequences that code for the two trypsin sensitive sites in the 130 kD toxin protein are the Arginine (Arg) amino acids at nucleotides 241 and 1963. These positions were determined by sequencing the trypsin-activated protein at both the N and C-termini. The N-terminal sequence was NH2-Ile-Glu-Thr-Gly-Tyr-Thr-Pro-Ile—. The amino acid sequence of isolated proteins is determined sequentially from the amino terminus using the standard Edman degradation technique with an Applied Biosystems Model 470A Gas Phase Protein Sequenator. The degradation products are converted to PTH-amino acid derivatives for identification by reverse phase high performance liquid chromatography. Carboxy terminal amino acid sequence has been determined by both the standard carboxy-peptidase digestion techniques and by the purification of the carboxy terminal tryptic fragment with subsequent Edman degradation from its amino terminus as above. These sequences were then compared to the amino acid sequences predicted from the nucleic acid sequence information.

6. Generation of a Truncated and More Active BTK Toxin Protein

Crystals of the BTK toxin were purified through repeated renograffin gradients. About 10 mg of the 130 kD crystal protein was resuspended in 1 ml of 20 mM Tris (pH 8.9) and about 10 microliters of 10N NaOH was added per ml of protein solution to bring the pH to 10.5 to 11.5. Dithiothreitol was added to 20 mM and then the solution was centrifuged to remove insoluble material. The supernatant was placed in dialysis tubing with a molecular cutoff of 2000 and dialyzed against 50 mM CHES (pH 9.4) for more than 10 hours in the cold. The dialyzed solubilized BTK crystal protein is referred to as "Ks."

The Ks is then treated with the protease trypsin in the ratio of 125 micrograms of trypsin per 10 mg of Ks. The digestion is stopped with 200 micrograms of PMSF to inactivate the trypsin. The material is then dialyzed against 20 mM Tris (pH 8.9) and purified by high performance liquid chromatography. The purified protein migrates in denaturing polyacrylamide gels as would a polypeptide of about 55-60 kD compared to appropriate standards. The activated toxin, referred to as "Kst," has an activity against T. ni. in the diet incorporation assay that is at least five-times as great as the untreated control, Ks, on an equivalent weight basis. The activation is demonstrated in the toxicity data in the following table, where the average weight of the larvae is plotted against the amount of material included in the diet.

TABLE 4

| TOXICITY OF ACTIVATED BTK CRYSTAL PROTEIN | | |
|---|---|---|
| Sample | Micrograms of toxin per well | Weight per larvae (mg) |
| Ks | 1.0 | 40 |
|  | 2.4 | 38 |
|  | 7.0 | 20 |
|  | 20 | 11 |
|  | 60 | 4 |
|  | 180 | 2 |
| Kst | 0.10 | 40 |
|  | 0.24 | 40 |
|  | 0.70 | 14 |
|  | 2.2 | 6 |
|  | 7.0 | 3 |
|  | 20 | 2 |

The results in Table 4 are consistent with the published experiments that used insect gut juice protease to activate the toxin by about four-fold (Tojo and Aizawa, Applied and Environmental Microbiology, 45:576–580, 1983). (However, see the finding of Nagamatsu et al. (Agric. Biol. Chem., 48:611–619, 1984) who also used trypsin to attempt activation of the toxin protein from Bacillus thuringiensis subsp. dendrolimus but reported no activation.) Further, protease digestion of the Ks material to achieve further degradation of the 55–60 kD polypeptide, showed no toxin material with molecular weights below about 20 kD.

7. Site-Directed Mutagenesis

Figure 4:
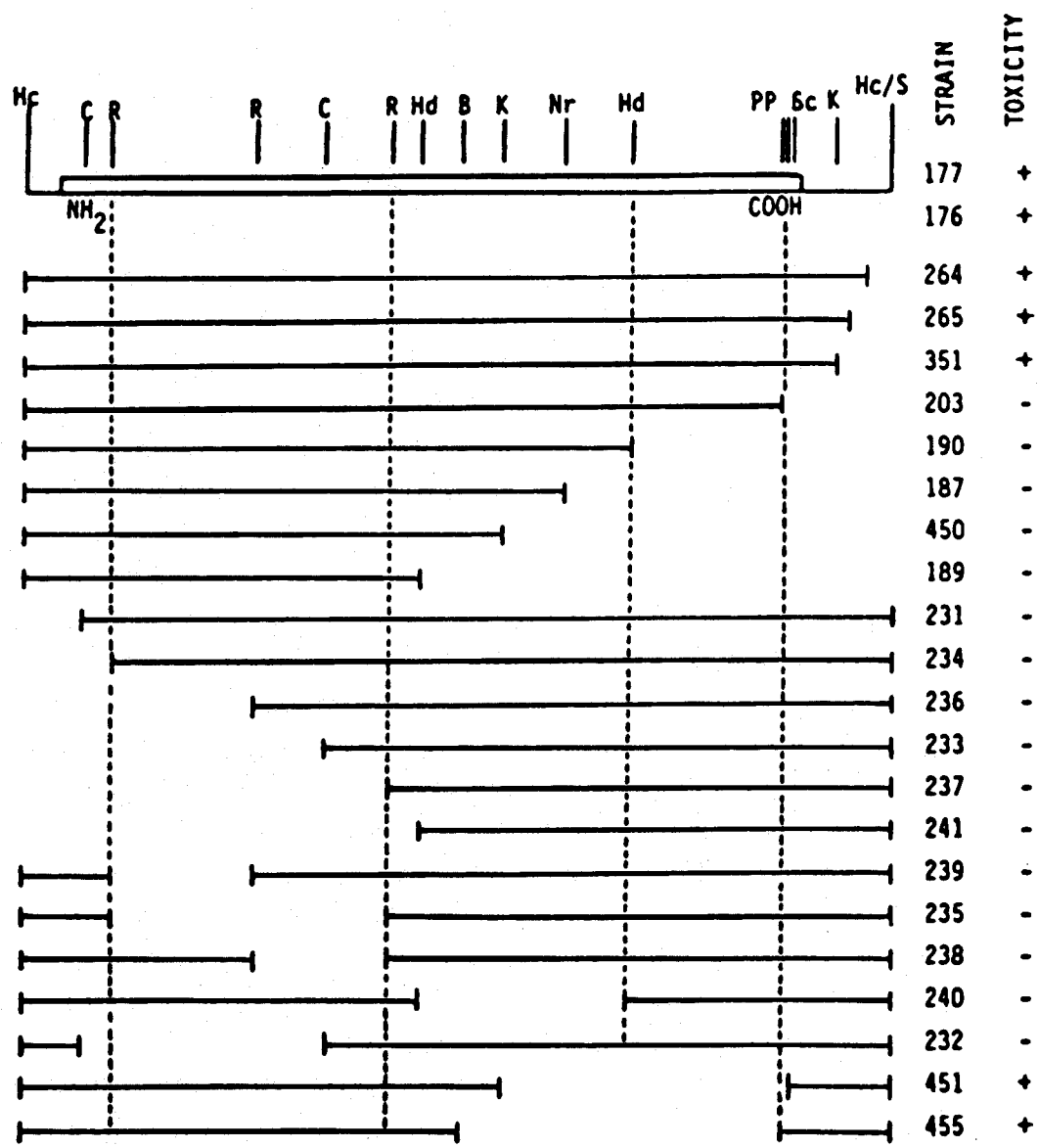
FIG. 4 is a diagram of several Bal31 deletions of the BTK structural gene. The gaps in the single line indicate deleted sequences. The restriction sites are abbreviated as follows: Hc=HincII, Nd=NdeI, Xm=XmnI, C=ClaI, R=EcoRI, Xb=XbaI, B=BclI, K=KpnI, Nr=NruI, Sc=ScaI, P=PvuII, Sal=SalI. $NH_2$=amino terminus and COOH= carboxy terminus. The toxicity of the proteins produced by each stream is indicated by the + (toxic) and − (non-toxic) symbols.

A series of site-specific deletion mutations were generated to locate the extent of the region of the structural gene that is essential for toxin activity. The deletions were constructed using restriction endonucleases and the exonuclease Bal31. The regions of the BTK structural gene that remain after the mutagenesis are depicted in FIG. 4 as lines and the deleted sequences as spaces. The toxicity is indicated to the right.

Cell extracts made from mutants with deletions that remove parts of the left half of the gene and the control sequences are not toxic, even when functional control sequences (the bacteriophase Lambda rightward promoter and ribosome binding site) are positioned exactly in frame to express the mutant gene product. An internal deletion between the leftmost pair of EcoRI restriction sites does not change the normal translational reading frame and causes the synthesis of a correspondingly shortened polypeptide, but it is not toxic. A paper presented by H. Whiteley at the 1984 Spores Conference at Asilomar, California demonstrated that deletion of the sequences that code for the first 9-10 amino acids at the amino terminal end of the BTK gene does not affect toxicity. However, a similar deletion that removes sequences that code for the first 49-50 amino acids at the amino terminal end does reduce the toxic activity. The deletions were generated using the sites for the XmnI restriction enzyme. The endpoints of these two deletions flank the region in the gene that codes for the trypsin sensitive site.

The loss of activity for mutants that have deletions in the C-terminal half of the BTK toxin gene can be reversed by joining the remaining sequences to the extreme C-terminal region of the BTK gene. Deletions that remove the sequences between the rightmost Kpn and HincII restriction sites remain as toxic as in the case of the parent construction, pSY177. Deletions that remove sequences between the PvuII and HincII sites eliminate the toxicity. Also an internal deletion that removes the sequences between the two Kpn sites eliminates the toxicity. These three deletions define a C-terminal region of the BTK toxin gene that is essential for the accumulation of the toxin in these constructions. Thus, the toxicity can be specified by a combination of most of the amino-half of the protein and no more than about 250 base pairs from near the C-terminus of the gene. The complete gene is not required for toxicity.

A deletion of the internal segment from the carboxy half of the BTK toxin gene was constructed. A plasmid pSY313, that contains the BTK structural gene (described in more detail in section 8c) and two KpnI sites in the carboxy half of the gene, was digested with KpnI and the ends were ligated to remove the intervening fragment. Then the ScaI to SalI fragment from the extreme right end of the BTK gene was inserted at the single reconstructed KpnI site. This effectively removes the BTK sequences between the leftmost KpnI and ScaI sites (see restriction map above), but retains information from the extreme C-terminal region. As shown above, this retains toxicity, unlike pSY450, a construction lacking the C-terminus segment.

To further support the extent of permissible deletions, another deletion was constructed that removed the sequences between the internal BclI restriction site and the downstream PvuII site. The resulting structural gene approximates the gene that would code for the trypsin activated toxin protein.

8. Expression in Bacillus Subtilis (a) Construction of the shuttle vector pSY228. The chloramphenicol resistance gene from pC194 carried on an MboI-HpaII fragment of about 1000 base pairs was inserted into the E. coli vector pBR322 at the PvuII site. The resulting plasmid, pSY129, confers resistance to ampicillin, tetracycline and chloramphenicol. Plasmid DNA was isolated from Bacillus subtilis strain 1264 (Le Hegarat and Anagnostopoulos, Molec. Gen. Genet. (1977) 157:167-174), by CsCl-ethidium bromide equilibrium centrifugation. Two plasmids, pGY31 (11.7 kb) and pGY32 (5.5 kb) were present. This mixture was digested to completion with SalI restriction enzyme and the cohesive ends filled in using the Klenow polymerase reaction to give blunt ends. The fragments were ligated to pSY129 that had been linearized with the enzyme BalI, and a new plasmid obtained called pSY171 that was about 9.4 kb in length. The insertion length was about 4.4 kb. This plasmid is unstable and gives rise spontaneously to a deletion variant (pSY228) of about 7.4 kb in length. Approximately 2 kb of DNA was deleted: mainly from the insertion (1400 to 1700 bases) but also from the pSY129 plasmid (600-300 bases). The exact junction has not been cloned and sequenced. The common insertion in pSY171 and pSY228 carries a functional origin for replication and allows the shuttle vectors to replicate in both E. coli and B. subtilis. Both shuttle vectors confer resistance to ampicillin, tetracycline and chloramphenicol in E. coli and only the latter in Bacillus species.

(b) Insertion of the BTK gene into pSY228. The BamHI to AvaI fragments from pSY177 and pSY176 were inserted into the BamHI to AvaI region in the tetracycline resistance gene of plasmid pSY228, to yield plasmids pSY244 and pSY245. The former has the BTK gene oriented as in pSY177 with respect to the flanking and interrupted tetracycline resistance gene. Plasmid pSY245 is the opposite orientation.

(c) Insertion of promoters in front of the BTK toxin gene in pSY244. Promoter bearing fragments described below were gel purified, cohesive ends were filled in using the Klenow polymerase reaction and the blunt ended fragments were ligated to a partial NdeI digest of pSY244. Each ligation yields three possible points of insertion (3 NdeI sites in pSY244) and two possible orientations, one of which is correct for BTK expression. Transformants were screened by restriction nuclease mapping to identify the proper constructions. The promoter for the B. subtilis "43" gene was removed from plasmid pSY243 (also referred to as pGR71-43 in Doi et al., Nature (1981) 293:309-311) on a fragment of about 471 base pairs by restricting with HindIII or on a fragment of about 420 base pairs by restricting with HindIII and RsaI. The former carries a promoter, ribosome binding site and the start of the "43" structural gene. The latter fragment carries only the promoter. The promoter for the B. subtilis ctc gene was removed from pSY277 (also referred to as pM1798 in Tatti and Moran, J. Molec. Biol. (1984) 175:285-297) on a 130 base pair fragment by restricting with EcoRI and SalI. The promoter for the B. subtilis veg gene was removed from pSY275 (also referred to as pMS480 in Moran et al., Molec. Gen. Genet. (1982) 186:339-340) by restricting with EcoRI and BamHI. The promoter for the B. subtilis spoVG gene was removed from pSY276 (also referred to as pCB1291 in Rosenbush et al., J. Bacteriology (1981) 148:341-351) by restricting with HindIII and EcoRI.

(d) Amount of toxin protein accumulated by promoter substitution variants: pSY313 (43), pSY452 (ctc), pSY453 (veg), pSY454 (spoVG). A time course of accumulation of the 130 kD toxin protein was made employing denaturing SDS polyacrylamide gels. Samples of cultures growing in shake flasks at 37° C. were withdrawn at different times and the optical density of the culture was measured. The cells were lysed by sonication and the proteins were denatured by boiling for four minutes in 1% SDS and 0.1% mercaptoethanol. Extracts from a constant number of cells were layered in each lane of the denaturing SDS polyacrylamide gels. After electrophoresis the gels were stained with Coomassie dye to detect the proteins. The results are reported as in the following table.

TABLE 5
AMOUNT OF 130 KD PROTEIN ACCUMULATED IN PROMOTER VARIANTS

| Plasmid Name | Substituted Promoter | Percent of Total Cell Protein as 130 KD* |
|---|---|---|
| pSY244 | Normal BTK | 1 |
| pSY313 | 43 | 3 |
| pSY452 | ctc | 10 |
| pSY453 | veg | 3 |
| pSY454 | VG | 25 |

*Determined at 6 hr after culture had switched from log-phase growth to stationary phase.

It is evident from the above results that the subject invention provides for a wide variety of novel polypeptide toxins based on naturally occurring polypeptide toxins, as well as methods for the production of such toxins. By employing the constructions of the subject invention, enhanced production of toxins can be obtained, so that the organisms may be used directly as the insecticide, where on a weight basis, substantially enhanced activity is achieved. Therefore, the subject methods provide for economic and efficient processes for novel polypeptide toxins. In addition, DNA constructions are prepared and provided employing heterologous promoters which result in efficient production of the desired toxins. Finally, activity of the toxin may be greatly enhanced by preparing the 130 kD toxin from the complete gene and subjecting it to mild protease digestion to produce fragments having substantially enhanced activity.

Although the foregoing invention has been described in some detail by way of illustration and example for purposes of clarity of understanding, it will be obvious that certain changes and modifications may be practiced within the scope of the appended claims.

What is claimed is:

1. A method for producing *B. thuringiensis* delta-endotoxin in enhanced amounts which comprises:
   growing transformed *E. coli* in an appropriate nutrient medium, wherein said *E. coli* are transformed with an expression vector containing the intact structural gene encoding said delta-endotoxin and 3' and 5' flanking regions which do not extend beyond the proximal HincII sites; and
   isolating the expressed delta-endotoxin.

2. A method according to claim 1, wherein said 3'-flanking region is less than about 300 bp, and the 5'-flanking region extends to the 5'-upstream HincII site.

3. A method according to claim 2, wherein said 3'-flanking region is at least partially removed with an exonuclease from said HincII cleavage site, and the 5'-flanking region extends to the 5'-upstream HincII site.

4. A DNA fragment containing the intact structural gene encoding the delta-endotoxin of *B. thuringiensis* and 3' and 5' flanking regions which do not extend beyond the proximal HincII sites.

5. A DNA construct comprising an *E. coli* replicon and a DNA fragment according to claim 4.

6. A DNA construct according to claim 5, wherein said replicon is derived from pBR322.

7. *E. coli* transformed with a construct according to claim 5.

* * * * *